US007419957B2

(12) United States Patent
Hwu et al.

(10) Patent No.: US 7,419,957 B2
(45) Date of Patent: Sep. 2, 2008

(54) PEPTIDES OF MELANOMA ANTIGEN AND THEIR USE IN DIAGNOSTIC, PROPHYLACTIC AND THERAPEUTIC METHODS

(75) Inventors: Patrick Hwu, Houston, TX (US); Rejean LaPointe, Laval (CA); Steven A. Rosenberg, Potomac, MD (US); Maria Parkhurst, Ellicott City, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 519 days.

(21) Appl. No.: 10/486,989

(22) PCT Filed: Aug. 22, 2002

(86) PCT No.: PCT/US02/26957

§ 371 (c)(1), (2), (4) Date: May 14, 2004

(87) PCT Pub. No.: WO03/018610

PCT Pub. Date: Mar. 6, 2003

(65) Prior Publication Data

US 2005/0065077 A1 Mar. 24, 2005

Related U.S. Application Data

(60) Provisional application No. 60/314,183, filed on Aug. 22, 2001.

(51) Int. Cl.
*A61K 38/00* (2006.01)
*A61K 39/395* (2006.01)
(52) U.S. Cl. ........................................ 514/13; 530/326
(58) Field of Classification Search ....................... None
See application file for complete search history.

(56) References Cited

U.S. PATENT DOCUMENTS

| 5,262,177 | A | | 11/1993 | Brown et al. |
| 5,399,346 | A | | 3/1995 | Anderson et al. |
| 5,844,075 | A | | 12/1998 | Kawakami et al. |
| 5,874,560 | A | * | 2/1999 | Kawakami et al. ......... 536/23.5 |
| 5,994,523 | A | | 11/1999 | Kawakami et al. |
| 6,537,560 | B1 | | 3/2003 | Kawakami et al. |

FOREIGN PATENT DOCUMENTS

| EP | 0 563 485 A1 | | 10/1993 |
| WO | WO 93/20185 A1 | | 10/1993 |
| WO | 01/90197 | * | 11/2001 |
| WO | WO 02/080848 | * | 10/2002 |

OTHER PUBLICATIONS

Kirkin et al, (1998, APMIS, 106 : 665-679).*
George et al. (2005, Trends in Immunology 26(12):653-659).*
Smith (1994, Clin Immunol, 41(4):841-849).*
Ezzell (J. NIH Res, 1995, 7:46-49).*
Spitler (Cancer Biotherapy, 1995, 10:1-3).*
Roitt et al, 1998, Immunology, 4th ed, Mosby, London, (p. 7.7-7.8).*
Holmes (Exp. Opin.Invest. Drugs, 2001, 10(3):511-519) (p. 7.7-7.8).*
Lapointe et al. (2001, J. of Immunol. 167(8):4758-64).*
Anichini et al., "Melanoma Cells and Normal Melanocytes Share Antigens Recognized by HLA-A2-Restricted Cytotoxic T Cell Clones from Melanoma Patients," *J. Exp. Med.*, 177, 989-998 (1993).
Barth et al., "Interferon γ and Tumor Necrosis Factor Have a Role in Tumor Regressions Mediated by Murine CD8+ Tumor-Infiltrating Lymphocytes," *J. Exp. Med.*, 173, 647-658 (1991).
Brichard et al., "The Tyrosinase Gene Codes for an Antigen Recognized by Autologous Cytolytic T Lymphocytes on HLA-A2 Melanomas," *J. Exp. Med.*, 178, 489-495 (1993).
Cerundolo et al., "Presentation of Viral Antigen Controlled by a Gene in the Major Histocompatibility Complex," *Nature*, 345, 449-452 (1990).
Chen et al., "Cancer-Testis Antigens: Targets for Cancer Immunotheraphy," *Cancer J. Sci. Am.*, 5, 16-17 (1999).
Chicz et al., "Specificity and Promiscuity among Naturally Processed Peptides Bound to HLA-DR Alleles," *J. Exp. Med.*, 178, 27-47 (1993).
Cormier et al., "Heterogeneous Expression of Melanoma-Associated Antigens and HLA-A2 in Metastatic Melanoma In Vivo," *Int. J. Cancer*, 75, 517-524 (1998).
Coulie et al., "Precursor Frequency Analysis of Human Cytolytic T Lymphocytes Directed Against Autologous Melanoma Cells," *Int. J. Cancer*, 50, 289-297 (1992).
Darrow et al., "The Role of HLA Class I Antigens in Recognition of Melanoma Cells by Tumor-Specific Cytotoxic T Lymphocytes: Evidence for Shared Tumor Antigens," *J. Immunol.*, 142(9), 3329-3335 (1989).
Dudley et al., "Antitumor Immunization with a Minimal Peptide Epitope (G9-209-2M) Leads to a Functionally Heterogeneous CTL Response," *J. Immunother.*, 22(4), 288-298 (1999).
GenBank Accession No. M32295.
Hom et al., "Common Expression of Melanoma Tumor-Associated Antigens Recognized by Human Tumor Infiltrating Lymphocytes: Analysis by Human Lymphocyte Antigen Restriction," *J. Immunother.*, 10, 153-164 (1991).
Hom et al., "Specific Release of Cytokines by Lymphocytes Infiltrating Human Melanomas in Response to Shared Melanoma Antigens," *J. Immunother.*, 13(1), 18-30 (1993).
Itoh et al., "Interleukin 2 Activation of Cytotoxic T-Lymphocytes Infiltrating into Human Metastatic Melanomas," *Cancer Res.*, 46, 3011-3017 (1986).
Kawakami, et al., "Identification of a Human Melanoma Antigen Recognized by Tumor-Infiltrating Lymphocytes Associated with in vivo Tumor Rejection," *Proc. Natl. Acad. Sci. USA*, 91, 6458-6462 (1994).

(Continued)

*Primary Examiner*—Sheela J Huff
(74) *Attorney, Agent, or Firm*—Leydig, Voit & Mayer

(57) ABSTRACT

Immunogenic peptides of a melanoma antigen recognized by T cells, designated gp100, bioassays using the peptides to diagnose, assess or prognose a mammal afflicted with cancer, more specifically melanoma or metastatic melanoma, and use of the proteins and peptides as immunogens to inhibit, prevent or treat melanoma.

8 Claims, 3 Drawing Sheets

OTHER PUBLICATIONS

Kawakami et al., "Interleukin 4 Promotes the Growth of Tumor-Infiltrating Lymphocytes Cytotoxic for Human Autologous Melanoma," *J. Exp. Med.*, 168, 2183-2191 (1988).

Kawakami et al., "IL-4 Regulates IL-2 Induction of Lymphokine-Activated Killer Activity From Human Lymphocytes," *J. Immunol.*, 142(10), 3452-3461 (1989).

Kawakami et al., "Shared Human Melanoma Antigens: Recognition by Tumor-Infiltrating Lymphocytes in HLA-A2.1-Transfected Melanomas," *J. Immunol.*, 148(2), 638-643 (1992).

Kawakami et al., "T-Cell Recognition of Human Melanoma Antigens," *J. Immunother.*, 14, 88-93 (1993).

Kershaw et al., "Generation of Gene-Modified T Cells Reactive Against the Angiogenic Kinase Insert Domain-Containing Receptor (KDR) Found on Tumor Vasculature," *Hum. Gene Ther.*, 11, 2445-2452 (2000).

Lapointe et al., "Human Dendritic Cells Require Multiple Activation Signals for the Efficient Generation of Tumor Antigen-Specific T Lymphocytes," *Eur. J. Immunol.*, 30, 3291-3298 (2000).

Malcherek et al., "Supermotifs Enable Natural Invariant Chain-Derived Peptides to Interact with Many Major Histocompatibility Complex-Class II Molecules," *J. Exp. Med.*, 181, 527-536 (1995).

Mata et al., "Th1 T Cell Responses to HIV-1 Gag Protein Delivered by a *Listeria monocytogenes* Vaccine Are Similar to Those Induced by Endogenous Listerial Antigens," *J. Immunol.*, 163, 1449-1456 (1999).

Matloubian et al., "CD4+ T Cells Are Requied To Sustain CD8$^+$ Cytotoxic T-Cell Responses during Chronic Viral Infection," *J. Virol.*, 68(12), 8056-8063 (1994).

Muul et al., "Identification of Specific Cytolytic Immune Responses Against Autologous Tumor in Humans Bearing Malignant Melanoma," *J. Immunol.*, 138(3), 989-995 (1987).

Naviaux et al., "The pCL Vector System: Rapid Production of Helper-Free, High-Titer, Recombinant Retroviruses," *J. Virol.*, 70(8), 5701-5705 (1996).

O'Neil et al., "Detection of Shared MHC-Restricted Human Melanoma Antigens After Vaccinia Virus-Mediated Transduction of Genes Coding for HLA," *J. Immunol.*, 151(3), 1410-1418 (1993).

Ossendorp et al., "Specific T Helper Cell Requirement for Optimal Induction of Cytotoxic T Lymphocytes Against Major Histocompatibility Complex Class II Negative Tumors," *J. Exp. Med.*, 187(5), 693-702 (1998).

Pardoll et al., "The Role of CD4+ T Cell Responses in Antitumor Immunity," *Curr. Opin. Immunol.*, 10, 588-594 (1998).

Parkhurst et al., "Improved Induction of Melanoma-Reactive CTL with Peptides From the Melanoma Antigen gp100 Modified at HLA-A*0201-Binding Residues," *J. Immunol.*, 157, 2539-2548 (1996).

Parry et al., "Autoreactivity Versus Autoaggression: A Different Perspective on Human Autoantigens," *Curr. Opin. Immunol.*, 10, 663-668 (1998).

Rammensee et al., "MHC Ligands and Peptide Motifs: First Listing," *Immunogenetics*, 41, 178-228 (1995).

Reeves et al., "Retroviral Transduction of Human Dendritic Cells with a Tumor-Associated Antigen Gene," *Cancer Res.*, 56, 5672-5677 (1996).

Rosenberg et al., "Immunologic and Therapeutic Evaluation of a Synthetic Peptide Vaccine for the Treatment of Patients with Metastatic Melanoma," *Nat. Med.*, 4(3), 321-327 (1998).

Rosenberg, "Karnofsky Memorial Lecture. The Immunotherapy and Gene Therapy of Cancer," *J. Clin. Oncol.*, 10(2), 180-199 (1992).

Rosenberg et al., "Immunization of Cancer Patients Using Autologous Cancer Cells Modified by Insertion of the Gene for Tumor Necrosis Factor," *Hum. Gene Ther.*, 3, 57-73 (1992).

Rosenberg et al., "Immunization of Cancer Patients Using Autologous Cancer Cells Modified by Insertion of the Gene for Interleukin-2," *Hum. Gene Ther.*, 3, 75-90 (1992).

Rosenberg et al., "A New Approach to the Adoptive Immunotherapy of Cancer with Tumor-Infiltrating Lymphocytes," *Science*, 233, 1318-1321 (1986).

Rosenberg et al., "Use of Tumor-Infiltrating Lymphocytes and Interleukin-2 in the Immunotherapy of Patients with Metastatic Melanoma: A Preliminary Report," *N. Engl. J. Med.*, 319, 1676-1680 (1988).

Salgaller et al., "Immunization Against Epitopes in the Human Melanoma Antigen gp100 following Patient Immunization with Synthetic Peptides," *Cancer Res.*, 56, 4749-4757 (1996).

Sensi et al., "T Cell Receptor (TCR) Structure of Autologous Melanoma-Reactive Cytotoxic T Lymphocyte (CTL) Clones: Tumor-Infiltrating Lymphocytes Overexpress In Vivo the TCR β Chain Sequence Used by an HLA-A2-Restricted and Melanocyte-Lineage-Specific CTL Clone," *J. Exp. Med.*, 178, 1231-1246 (1993).

Surman et al., "Cutting Edge: CD4+ T Cell Control of CD8+ T Cell Reactivity to a Model Tumor Antigen," *J. Immunol.*, 164, 562-565 (2000).

Topalian et al., "Human CD4$^+$ T Cells Specifically Recognize a Shared Melanoma-Associated Antigen Encoded by the Tyrosinase Gene," *Proc. Natl. Acad. Sci, USA*, 91, 9461-9465 (1994).

Topalian et al., "Tumor-Specific Cytolysis by Lymphocytes Infiltrating Human Melanomas," *J. Immunol.*, 142, 3714-3725 (1989).

Touloukian et al., "Identification of a MHC Class II-Restricted Human gp100 Epitope Using DR4-IE Transgenic Mice," *J. Immunol.*, 164, 3535-3542 (2000).

Traversari et al., "A Nonapeptide Encoded by Human Gene MAGE-1 is Recognized on HLA-A1 by Cytolytic T Lymphocytes Directed Against Tumor Antigen MZ2-E," *J. Exp. Med.*, 176, 1453-1457 (1992).

Van Der Bruggen et al., "A Gene Encoding an Antigen Recognized by Cytolytic T Lymphocytes on a Human Melanoma," *Science*, 254, 1643-1647 (1991).

Zajac et al., "Viral Immune Evasion Due to Persistence of Activated T Cells Without Effector Function," *J. Exp. Med.*, 188(12), 2205-2213 (1998).

Zemmour et al., "HLA Class I Nucleotide Sequences, 1992," *Tissue Antigens*, 40, 221-228 (1992).

Zeng et al., "Identification of CD4$^+$ T Cell Epitopes from NY-ESO-1 Presented by HLA-DR Molecules," *J. Immunol.*, 165, 1153-1159 (2000).

\* cited by examiner

PEPTIDES OF MELANOMA ANTIGEN AND THEIR USE IN DIAGNOSTIC, PROPHYLACTIC AND THERAPEUTIC METHODS

This application is the U.S. national phase of PCT/US02/26957, which was filed on Aug. 22, 2002 and which claims the benefit of U.S. provisional patent application Ser. No. 60/314,183, which was filed on Aug. 22, 2001.

FIELD OF THE INVENTION

This invention is in the field of the treatment of human cancers. More specifically, this invention relates to genes encoding melanoma antigens recognized by T cells and their corresponding proteins and peptides and to diagnostic, prophylactic, and therapeutic applications which employ these genes, proteins, and peptides.

BACKGROUND OF THE INVENTION

Melanomas are aggressive, frequently metastatic tumors derived from either melanocytes or melanocyte related nevus cells ("Cellular and Molecular Immunology" (1991) (eds) Abbas A. K., Lechtman, A. H., Pober, J. S.; W. B. Saunders Company, Philadelphia: pages 340-341). Melanomas make up approximately three percent of all skin cancers and the worldwide increase in melanoma is unsurpassed by any other neoplasm, with the exception of lung cancer in women ("Cellular and Molecular Immunology" (1991) (eds) Abbas, A. K., Lechtiman, A. H., Pober, J. S.; W. B. Saunders Company Philadelphia pages: 340-342; Kirkwood and Agarwala, (1993) *Principles and Practice of Oncology* 7:1-16). Even when melanoma is apparently localized to the skin, up to 30% of the patients will develop systemic metastasis and the majority will die (Kirkwood and Agarwala, (1993) *Principles and Practice of Oncology* 7:1-16). Classic modalities of treating melanoma include surgery, radiation and chemotherapy. In the past decade immunotherapy and gene therapy have emerged as new and promising methods for treating melanoma.

T cells play an important role in tumor regression in most murine tumor models. Tumor infiltrating lymphocytes (TIL) that recognize unique cancer antigens can be isolated from many murine tumors. The adoptive transfer of these TIL plus interleukin-2 can mediate the regression of established lung and liver metastases (Rosenberg, S. A., et al., (1986) *Science* 233:1318-1321). In addition, the secretion of IFN-γ by injected TIL significantly correlates with in vivo regression of murine tumors, suggesting activation of T cells by the tumor antigens (Barth, R. J., et al., (1991) *J. Exp. Med.* 173:647-658). The known ability of tumor TIL to mediate the regression of metastatic cancer in 35 to 40% of melanoma patients when adoptively transferred into patients with metastatic melanoma attests to the clinical importance of the antigens recognized (Rosenberg, S. A., et al., (1988) *N. Enql. J. Med.* 319:1676-1680; Rosenberg, S. A., (1992) *J. Clin. Oncol.* 10:180-199).

T cell receptors on CD8$^+$ T cells recognize a complex consisting of an antigenic peptide (9-10 amino acids for HLA-A2), β-2 microglobulin and class I major histocompatibility complex (MHC) heavy chain (HLA-A, B, C, in humans). Peptides generated by digestion of endogenously synthesized proteins are transported into the endoplastic reticulum, bound to class I MHC heavy chain and β2 microglobulin, and finally expressed in the cell surface in the groove of the class I MHC molecule. Thus, T cells can detect molecules that originate from proteins inside cells, in contrast to antibodies that detect intact molecules expressed on the cell surface. Therefore, antigens recognized by T cells may be more useful than antigens recognized by antibodies.

Although emphasis is on CD8+ T cell responses, there is emerging support that CD4+ T cells may play an important role in anti-tumor immunity. As reviewed by Pardoll and Topalian (*Curr. Opin. Immunol.* 10:588, 1998), CD4+ T cells have been demonstrated in murine studies to exert helper activity through the induction of CD8+ T cells and B cells and further have both direct and indirect effects on tumor cells, including those deficient in MHC class II. In humans, CD4+ T cells play a critical role in the initiation of several autoimmune diseases (Parry et al., *Curr. Opin. Immunol.* 10:663, 1998) and in pathogenic resistance (Mata and Paterson, *J. Immunol.* 163:1449, 1999; Zajac et al., *J. Exp. Med.* 188: 2205, 1998). CD4+ T cells activated dendritic cells primarily through the interaction of CD40 and its ligand. There is growing support that the combination of MHC class I and class II epitopes derived from the same tumor antigen can enhance antitumor effector function and long-term immunity (Surman et al., *J. Immunol.* 164:562, 2000; Ossendorp et al., *J. Exp. Med.* 187:693, 1998; Matloubian et al., *J. Virol.* 68:8056, 1994).

Strong evidence that an immune response to cancer exists in humans is provided by the existence of lymphocytes within melanoma deposits. These lymphocytes, when isolated, are capable of recognizing specific tumor antigens on autologous and allogeneic melanomas in an MHC-restricted fashion (Itoh, K. et al. (1986), *Cancer Res.* 46: 3011-3017; Muul, L. M., et al. (1987), *J. Immunol.* 138:989-995); Topalian, S. L., et al., (1989) *J. Immunol.* 142: 3714-3725; Darrow, T. L., et al., (1989) *J. Immunol.* 142: 3329-3335; Hom, S. S., et al., (1991) *J. Immunother.* 10:153-164; Kawakami, Y., et al., (1992) *J. Immunol.* 148: 638-643; Hom, S. S., et al., (1993) *J. Immunother.* 13:18-30; and O'Neil, B. H., et al., (1993) *J. Immunol.* 151: 1410-1418). TIL from patients with metastatic melanoma recognize shared antigens including melanocyte-melanoma lineage specific tissue antigens in vitro (Kawakami, Y., et al., (1993) *J. Immunother.* 14: 88-93; Anichini, A. et al., (1993) et al., *J. Exp. Med.* 177: 989-998). Anti-melanoma T cells appear to be enriched in TIL, probably as a consequence of clonal expansion and accumulation at the tumor site in vivo (Sensi, M., et al., (1993) *J. Exp. Med.* 178:1231-1246). The fact that many melanoma patients mount cellular and humoral responses against these tumors and that melanomas express both MHC antigens and tumor associated antigens (TAA) suggests that identification and characterization of additional melanoma antigens will be important for immunotherapy of patients with melanoma.

The melanocyte differentiation antigen, gp100, is expressed in more than 75% of human melanomas (Cormier et al., *Int. J. Cancer* 75:517, 1998). Although the gp100 antigen is predominantly expressed intracellularly, it is a suitable immunogenic antigen. The intracellular proteins have been demonstrated to be processed and presented as peptides in the context of MHC molecules to immune system cells. In particular, TIL derived from tumors of melanoma patients have been identified and react with the gp100 antigen. Given that vaccination with a modified gp100 CD8+ T cell epitope combined with IL-2 reportedly resulted in a 42% response rate in patients with metastatic melanoma (Rosenberg et al., *Nat. Med.* 4:321, 1998; Parkhurst et al., *J. Immunol.* 157: 2539, 1996), only a few patients responded clinically to this particular vaccine regimen, and additionally, only transient responses were observed. Thus, in order to increase the immunogenicity and therapeutic efficacy of vaccines comprising gp100 CD8+ T cell epitopes, antigen-specific CD4+ T cells can be combined. Therefore, the gp100 MHC class I and class II epitopes can be useful for cellular responses against melanoma, and can also play a significant role in therapy and diagnosis of melanoma patients.

Peripheral blood lymphocytes have been used to identify several potential melanoma tumor antigens. For example, Van Der Bruggen et al. (*Science* 254: 1643-1647, 1991) has characterized a gene coding for a melanoma antigen, designated MAGE-1, using T cell clones established from the peripheral blood of patients who were repetitively immunized in vivo with mutagenized tumor cells. Cytotoxic T cells derived from the peripheral blood lymphocytes of patients with melanoma were used to identify a potential antigenic peptide encoding MAGE-1 (Traversari, C., et al. (1992) *J. Exp. Med.* 176:1453-1457). Brichard et al. ((1993) *J. Exp. Med.* 178:489-495) has also characterized a gene encoding a melanoma antigen designated tyrosinase using peripheral blood lymphocytes from patients who were sensitized by repetitive in vitro stimulation with tumor. Further support for the therapeutic potential of melanoma antigens is provided by Brown et al. (U.S. Pat. No. 5,262,177). Brown et al. (U.S. Pat. No. 5,262,177) relates to a recombinant vaccinia virus-based melanoma vaccine where the melanoma antigen p97 is reported to show a protective effect from tumor cell challenge in a murine model. Characterization of additional melanoma antigens can be important for the development of new strategies for cancer immunotherapy, in particular for melanoma.

SUMMARY OF THE INVENTION

This invention relates, in general, to peptides or variations of peptides derived from a melanoma-associated antigen known as gp100. In addition, the invention relates to methods of using the gp100 peptides or derivatives thereof for treating and preventing the progression of melanoma-associated diseases. Further, the gp100 peptides and variants thereof can be used as an immunogen for the treatment of patients in need thereof.

The present invention provides immunogenic peptides derived from a gp100 melanoma antigen protein sequence. For example, new peptides are exemplified by SEQ ID NOs: 2-21.

In addition, the present invention provides compositions or immunogens comprising all or part of the gp100 protein or peptides capable of eliciting an immune response in a mammal to melanoma antigens.

Further provided are diagnostic methods for human disease involving gp100 peptides or variants thereof, in particular for melanomas and metastatic melanomas.

Still further provided are therapeutic methods for the treatment of melanoma using all or part of the gp100 peptides, variants, vaccines or immunogens thereof.

Yet still further provided are methods of inhibiting or preventing the recurrence of melanoma in a subject in need thereof.

DETAILED DESCRIPTION OF THE INVENTION

Figure 1:
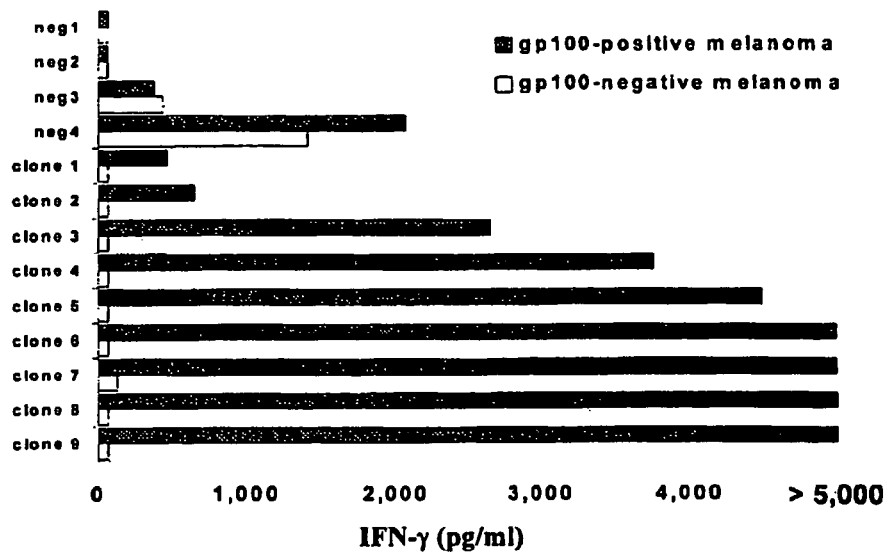
FIGS. 1A and 1B show the generation of HLA-DR-specific T cells using gp100-transduced dendritic cells (DC). Gp100-transduced DCs were used to stimulate autologous T cells in the presence of CD40L and lipopolysaccharide (LPS). After stimulating two times, the cultured T cells were cloned by limiting dilution and reactivity was assessed by recognition of autologous melanoma cells expressing gp100. (A) Reactivity of some representative clones is shown. (B) Reactivity of clones 6 and 8 against autologous (Auto) or HLA-DR unmatched EBV-B cells after pulsing with control protein (NY-ESO-1) or gp100 purified protein is shown. Antibodies blocking MHC class I (X-MHC cl I), MHC class II (X-MHC cl II) or HLA-DR (X-HLA-DR) recognition were added to the assay. Results are expressed in pg/ml of IFN-γ released following a 24 h co-culture. Legend: neg: negative.
Figure 1:
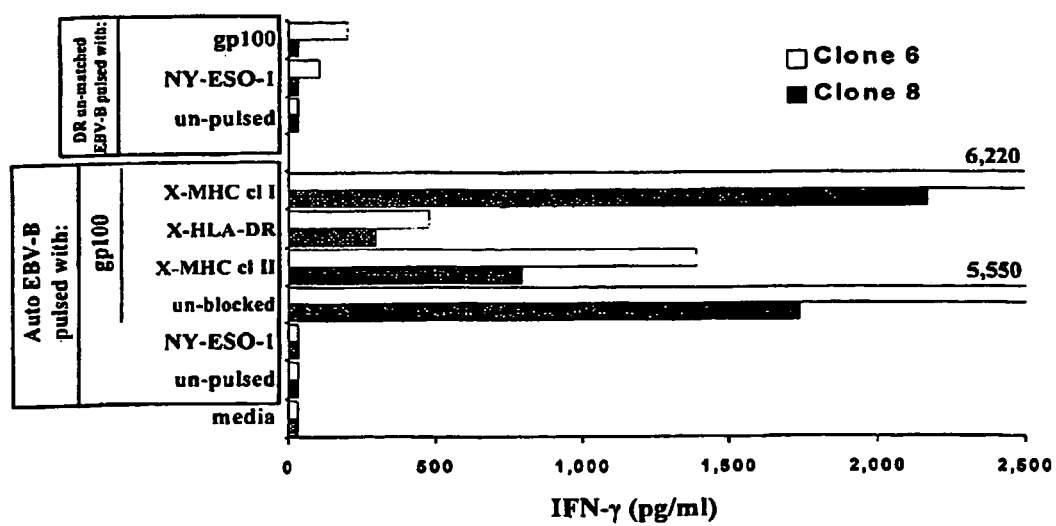

For the purpose of a more complete understanding of the invention, the following definitions are described herein. Nucleic acid sequences include, but are not limited to, DNA, RNA or CDNA, preferably gp100 nucleic acids. Gp100 messenger RNA (mRNA) refers to one or more RNA transcripts which are a product of the gp100 gene.

The term "melanoma" includes, but is not limited to, melanomas, metastatic melanomas, melanomas derived from either melanocytes or melanocyte-related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. Such melanomas in mammals may be caused by, chromosomal abnormalities, degenerative growth and developmental disorders, mitogenic agents, ultraviolet radiation (UV), viral infections, inappropriate tissue expression of a gene, alterations in expression of a gene, and presentation on a cell, or carcinogenic agents. The aforementioned melanomas can be diagnosed, assessed or treated by methods described in the present application.

"Atypical mole" means a mole with features that are abnormal and may be precancerous.

"Major Histocompatibility Complex" (MHC) is a generic designation meant to encompass the histo-compatibility antigen systems described in different species, including the human leukocyte antigens (HLA). Examples of MHC Class I genes that may be used include, but are not limited to, HLA-A, HLA-B and HLA-C genes. Examples of preferred MHC specificities or restriction types include, but are not limited to HLA-A1, HLA-A2, such as the HLA-A2.1 subtype, or HLA-A24 (Zemmour, J. et al. (1992) *Tissue Antigens* 40:221-228). Further, MHC Class II genes that are preferred include, but are not limited to, HLA-DR, HLA-DQ, and HLA-DP genes. Examples of more preferred MHC restriction types include, but are not limited to, HLA-DRβ1*0401, HLA-DRβ4-01, HLA-DRβ5-02, HLA-DRβ1-1601, and most preferably, HLA-DRβ1*0701, where 16-28% of the Caucasian and Hispanic population is HLA-DRβ1*0701.

The present invention relates to immunogenic peptides, variants, derivatives, or analogs thereof, from the gp100 protein, where the peptide has substantially the same function as the gp100 antigen or protein. Also encompassed by the invention are recombinant proteins encoded by all or part of a gp100 nucleic acid sequence. One skilled in the art would be knowledgeable of generating the gp100 proteins using methods commonly known. Such proteins or polypeptides include, but are not limited to, a fragment of the gp100 protein, or a substitution, addition, or deletion mutant of a gp100 protein. This invention also encompasses proteins or peptides that are substantially homologous to the gp100 melanoma antigen. "Substantially homologous" is defined herein as about 50-100% homology, preferably about 70-100% homology, and most preferably about 90-100% homology between the gp100 and any another amino acid sequence or protein or peptide. Proteins having greater than 98% homology and/or identity of sequence to gp100 (GenBank Accession No. M32295) are considered gp100 proteins and/or antigens.

An "immunogenic peptide" is defined herein as a peptide derived from the gp100 protein sequence or a gp100 protein sequence capable of causing a cellular or humoral immune response in a mammal. Further, the HLA-DRβ*0701-restricted gp100 immunogenic peptides of the invention have an amino acid sequence comprising 40 amino acids or fewer in length, preferably about 10 to 30 amino acids in length, and most preferably about 17-21 amino acids in length.

A preferred embodiment of the invention provides immunogenic gp100 peptides of at least about 40 amino acids or fewer be used, preferably about 40 amino acids or fewer in length, more preferably about 10-30 amino acids in length, and most preferably about 17-21 amino acids in length. A further embodiment of the invention provides an immunogenic gp100 peptide having a contiguous amino acid sequence of about 40 amino acids or less, comprising MLGTHTMEVTV (SEQ ID NO:1), TTEWVETTARELPIPE (SEQ ID NO:21), or a variant of either of the foregoing, said peptide is HLA-DRβ1*0701 restricted and induces an immune response. Some preferred examples of gp100 peptides of the invention comprise any of the following sequences: TGRAMLGTHTMEVTVYH (SEQ ID NO:2), LSIGTGRAMLGTHTMEVTVYH (SEQ ID NO:3), IGTGRAMLGTHTMEVTVYHRR (SEQ ID NO:4), TGRAMLGTHTMEVTVYHRRGS (SEQ ID NO:5), TGRAMLGTHTMEVTVYHR (SEQ ID NO:6), TGRAMLGTHTMEVTVYHRR (SEQ ID NO:7), TGRAMLGTHTMEVTVYHRRG (SEQ ID NO:8), GTGRAMLGTHTMEVTVYHRRG (SEQ ID NO:9), GTGRAMLGTHTMEVTVYH (SEQ ID NO:10), IGTGRAMLGTHTMEVTVYH (SEQ ID NO:11), SIGTGRAMLGTHTMEVTVYH (SEQ ID NO:12), SIGTGRAMLGTHTMEVTVYHR (SEQ ID NO:13), SGLSIGTGRAMLGTHTMEVTV (SEQ ID NO:14), RAMLGTHTMEVTVYHRRGSRS (SEQ ID NO:15), MLGTHTMEVTVYHRRGSRSYV (SEQ ID NO:16), TGRAFLGTHTMEVTVYHRRGS (SEQ ID NO:17), TGRALLGTHTMEVTVYHRRGS (SEQ ID NO:18), TGRAYLGTHTMEVTVYHRRGS (SEQ ID NO:19), PVSGLSIGTGRAMLGTHTMEV (SEQ ID NO:20), TTEWVETTARELPIPE (SEQ ID NO:21) and a variant thereof, wherein the peptide is capable of inducing an immune response in a mammal, in particular a human.

The term "variant" as defined herein, includes any peptide which displays the functional aspects of the immunogenic gp100 peptide. Any polypeptide having an amino acid residue sequence substantially identical to the gp100 sequence in which one or more residues have been conservatively substituted with a functionally similar residue and which displays the functional aspects of the gp100 antigen is considered to be a "variant." Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, or between glycine and serine, the substitution of one basic residue, such as lysine, arginine or histidine for another, or the substitution of one acidic residue, such as aspartic acid or glutamic acid for another.

The phrase "conservative substitution" also includes the use of a chemically derivatized residue in place of a non-derivatized residue. "Chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. Proteins or polypeptides of the present invention also include any polypeptide having one or more additions and/or deletions or residues relative to the sequence of a polypeptide whose sequence is encoded in the DNA of gp100.

In one embodiment of the invention, gp100 epitopes are determined and based upon a sequence motif. In order to generate immunogenic peptides for induction of a CD4+ T cell response, a variety of peptide epitopes were synthesized in which at least one amino acid position was changed based on the binding motifs of peptides presented by HLA-DRβ*0701 (Chicz et al., J. Exp. Med. 178:27-47, 1993; Rammensee, H. G. Immunogenetics 41:178-228, 1995). Amino acids at precise positions in the gp100 peptide sequence have been suggested as anchor residues to the MHC molecule. Also, the amino acid sequence in the groove of the MHC molecule corresponding to the contact zone with the peptide influences the composition of the anchor residues. MHC molecules are highly polymorphic in the population. The anchor residue motifs differ depending on the MHC proteins expressed.

Optimal anchor residues have been identified by sequencing several peptides bound to common MHC class I and class II molecules. For example, starting with the first amino acid bound to MHC-DR$_\beta$1*0701, anchor residues have been identified at position 1, 4, 6 and 9. Frequently, more than one amino acid with similar properties (charge, hydrophobicity, etc.) can be found for a particular anchor residue. However, these putative optimal anchor residues are not perfect and often, exceptions can be seen. Modifications according to the optimal defined binding motif can be made at putative anchor residues of a peptide in order to increase the affinity to the MHC class II molecule and its immunogenicity. The consensus motif of the present invention comprises: position 1 having a residue comprising Phe, Tyr, Trp, Ile, Leu, or Val; position 4 having a residue comprising Asp, Glu, His, Lys, Asn, Gln, Arg, Ser, Thr, or Tyr; position 6 having a residue comprising Asn, Ser, or Thr; and position 9 having a residue comprising Val, Ile, Leu, Tyr, or Phe, or derivatives thereof.

This invention also provides a recombinant DNA molecule comprising all or part of the gp100 nucleic acid sequence and a vector. Expression vectors suitable for use in the present invention comprise at least one expression control element operationally linked to the nucleic acid sequence. The expression control elements are inserted in the vector to control and regulate the expression of the nucleic acid sequence. Expression control elements and operational elements necessary or preferred for appropriate transcription and subsequent translation are used.

It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. It is also understood that the skilled artisan will be able to easily construct such vectors using conventional methods (Ausubel et al., (1987) in "Current Protocols in Molecular Biology", John Wiley and Sons, New York, N.Y.) or commercially available vectors. The host organism into which a recombinant expression vector containing all or part of the gp100 nucleic acid sequence has been inserted and the means by which the vector carrying the gene of interest is introduced into the cell are commonly known in the art (Sambrook et al., (1989) in "Molecular Cloning. A Laboratory Manual", Cold Spring Harbor Press, Plainview, N.Y.).

More specifically, a viral vector, such as a retroviral vector, can be introduced into mammalian cells. Examples of mammalian cells into which the retroviral vector can be introduced include, but are not limited to, primary mammalian cultures or continuous mammalian cultures, COS cells, NIH3T3, or 293 cells (ATTC #CRL 1573). The means by which the vector carrying the gene may be introduced into a cell includes, but is not limited to, microinjection, electroporation, transfection or transfection using DEAE dextran, lipofection, calcium phosphate or other procedures known to one skilled in the art (Sambrook et al. (EDS) (1989) in "Molecular Cloning. A laboratory manual", Cold Spring Harbor Press Plainview, N.Y.).

Another aspect of this invention relates to a host organism into which recombinant expression vector containing all or part of the gp100 nucleic acid sequence has been inserted. The host cells transformed with the gp100 nucleic acid sequence of this invention includes eukaryotes, such as animal, plant, insect and yeast cells and prokaryotes, such as *E. coli*. The means by which the vector carrying the gene may be introduced into the cell includes, but is not limited to, microinjection, electroporation, transduction, or transfection using DEAE-dextran, lipofection, calcium phosphate or other procedures known to one skilled in the art (Sambrook et al. (1989) in "Molecular Cloning. A Laboratory Manual", Cold Spring Harbor Press, Plainview, N.Y.).

"Melanoma antigen" or "immunogen" means all or part thereof of the gp100 protein or peptides based on the gp100 protein sequence capable of causing a cellular or humoral immune response in a mammal. Such antigens are also reactive with antibodies from animals immunized with all, part or parts of the gp100 protein.

In one embodiment of the invention, a composition that can induce an immune response or an immunogen is prepared using recombinant gp100 protein or peptide expression vectors. To provide an immune-response-inducing composition or an immunogen to an individual, a genetic sequence which encodes for all or part of the gp100 nucleic acid sequence is inserted into an expression vector, as described above, and introduced into the mammal to be immunized. Examples of vectors that may be used in the aforementioned immune-response-inducing compositions, such as vaccines, include, but are not limited to, defective retroviral vectors, adenoviral vectors, vaccinia viral vectors, fowl pox viral vectors, or other viral vectors (Mulligan, R. C., (1993) *Science* 260:926-932).

The immune-response-inducing composition or immunogen can be administered in accordance with conventional methods, alone or in combination with adoptive immunotherapy, e.g., T-cells generated against the gp100 epitope. For example, the immunogen can be used in a suitable diluent, such as saline or water, or complete or incomplete adjuvants. Further, the immunogen can be bound to a carrier to make the protein immunogenic. The immunogen also can be coupled with lipoproteins or administered in liposomal form or with adjuvants. The immunogen can be administered by any route, such as intravenous, intraperitoneal, intramuscular, subcutaneous, and the like. The immunogen can be administered once or at periodic intervals until a significant titer of anti-gp100 immune cells or anti-gp100 antibody is produced. The presence of anti-gp100 immune cells can be assessed by measuring the frequency of precursor CTL (cytotoxic T-lymphocytes) or CD4+ T cells against gp100 antigen prior to and after immunization by a CTL precursor analysis assay (Coulie, P. et al., (1992) *International Journal Of Cancer* 50:289-297). Antibodies can be detected in the serum using the immunoassay described above.

In yet another embodiment of this invention, multivalent immune-response-inducing compositions, e.g., vaccines, or immunogens against one or more melanoma antigens are provided. Such multivalent compositions can comprise all or part of the gp100 protein peptides or analogs, or combinations thereof.

In a further embodiment of this invention, the recombinant or natural gp100 protein, peptides, or analogs thereof, and/or pharmaceutical compositions or formulations comprising the recombinant or natural gp100 protein, peptides, or analogs thereof, can be used as an immune-response-inducing composition or an immunogen in a therapeutic or preventative manner. When provided prophylactically, the immune-response-inducing composition or immunogen is provided in advance of any evidence of melanoma. The prophylactic administration of the gp100 immune-response-inducing composition or immunogen serves to inhibit, prevent or attenuate melanoma in a mammal. In a preferred embodiment, a method of treating a cancer, such as melanoma, in a mammal comprising administering an immune-response-inducing composition or immunogen having one or more gp100 peptides. The immune-response-inducing composition or immunogen can be provided as a pharmaceutical composition comprising an immunogenic peptide having a contiguous gp100 amino acid sequence of 40 amino acids or less, comprising MLGTHTMEVTV (SEQ ID NO:1) or a variant thereof, or any of SEQ ID NOs:2-21, in an amount effective to stimulate or induce an immunotherapeutic response. Additionally, a method of inhibiting or preventing a recurrence of, for example, melanoma cancer in a mammal by administering an immune-response-inducing composition or immunogen comprising one or more gp100 peptides. Preferably, the immunogen is provided as a pharmaceutical composition comprising an immunogenic peptide having a contiguous gp100 amino acid sequence of 40 amino acids or less, comprising MLGTHTMEVTV (SEQ ID NO:1) or a variant thereof, or any of SEQ ID NOs:2-21, or variants thereof, in an amount effective to stimulate or induce an immunoprophylactic response.

More specifically, when provided prophylactically, the immunogen is provided in advance of any evidence or in advance of any symptom due to melanoma or after surgical resection of a tumor to prevent recurrence. Preferably, the immunogen is prophylactically administered in an effective amount ranging from about 0.01-100 mg per patient per dose. The prophylactic administration of the immunogen serves to inhibito, prevent or attenuate melanoma in a mammal. Examples of such mammals include, but are not limited to, humans with a family history of melanoma, humans with a history of atypical moles, humans with a history of FAM-M syndrome or humans afflicted with melanoma previously resected and, therefore, at risk for reoccurrence.

In yet another embodiment, the immune-response-inducing composition, e.g., vaccine, or immunogen, when provided therapeutically, is provided to enhance the patient's own immune response to the tumor antigen present on the melanoma or metastatic melanoma. The immune-response-inducing composition, which acts as an immunogen, may be obtained from various sources, including, for example, a cell, a cell lysate from cells transfected with a recombinant expression vector, a cell lysate from cells transfected with a gp100 recombinant expression vector, or a culture supernatant containing the expressed protein. Alternatively, the immunogen may be a partially or substantially purified gp100 protein, peptide or analog thereof produced naturally, recombinantly, or synthetically. The proteins or peptides may be conjugated with lipoprotein or administered in liposomal form or with adjuvant. Further, the immunogen may be provided at (or shortly after) the onset of the disease or at the onset of any symptom of the disease. Preferably, the immunogen is therapeutically administered in an effective amount ranging from 0.01 to 100 mg per patient per dose. The therapeutic administration of the immunogen serves to attenuate the disease. In a preferred embodiment of the invention, the gp100 immunogenic peptides may be used for the therapeutic and adjuvant (prevention of recurrent cancers) treatment of melanomas and are not limited to subjects expressing the MHC Class II molecule DRβ*0701, as Class II-restricted peptides are often capable of binding to more than one Class II molecule (Chicz et al. *J. Exp. Med.* 178:27-47, 1993; Malcherek et al. *J. Exp. Med.* 181:527-536, 1995).

TABLE 1

Gp100 Peptide Identification (IFN-γ; pg/ml)

| gp100 | | | 50 μm | 10 μm | SEQ ID NO: |
|---|---|---|---|---|---|
| 170-190 | LSIG TGRAMLG | THTMEVTVYH | >25,000 | 21,000 | 3 |
| 168-188 | SGLSIG TGRAMLG | THTMEVTV | 4,200 | 1,655 | 14 |
| 166-186 | PVSGLSIG TGRAMLG | THTMEV | 19 | <8 | 20 |
| 172-192 | IG TGRAMLG | THTMEVTVYH RR | >25,000 | 17,050 | 4 |
| 174-194 | TGRAMLG | THTMEVTVYH RRGS | >25,000 | 17,140 | 5 |
| 176-196 | RAMLG | THTMEVTVYH RRGSRS | 15,230 | 912 | 15 |
| 178-198 | MLG | THTMEVTVYH RRGSRSYV | 5,940 | 52 | 16 |
| | TGRAMLG | THTMEVTVYH | >25,000 | 14,010 | 2 |
| | TGRAMLG | THTMEVTVYH R | >25,000 | 11,100 | 6 |
| | TGRAMLG | THTMEVTVYH RR | >25,000 | 11,550 | 7 |
| | TGRAMLG | THTMEVTVYR RRG | >25,000 | 17,910 | 8 |
| | G TGRAMLG | THTMEVTVYH RRG | >25,000 | 22,910 | 9 |
| | G TGRAMLG | THTMEVTVYH | >25,000 | 18,770 | 10 |
| | IG TGRAMLG | THTMEVTVYH | >25,000 | 17,590 | 11 |
| | SIG TGRAMLG | THTMEVTVYH | >25,000 | 20,710 | 12 |
| | SIG TGRAMLG | THTMEVTVYH R | >25,000 | 12,210 | 13 |
| | TGRAFLG | THTMEVTVYH RRGS | >25,000 | 19,390 | 17 |
| | TGRALLG | THTMEVTVYH RRGS | >25,000 | 23,140 | 18 |
| | TGRAYLG | THTMEVTVYH RRGS | >25,000 | 11,640 | 19 |
| | | Un-pulsed | | <8 | |
| | NY-ESO-1 | (0.14 um) | | <8 | |
| | gp100 | (0.14 um) | | 13,730 | |

In addition to use as an immune-response-inducing composition, e.g., vaccine, or an immunogen of the invention, the pharmaceutical compositions can be used to prepare antibodies to gp100 antigen, peptides or analogs thereof. The antibodies can be used directly as anti-melanoma agents. To prepare antibodies, a host animal is immunized using the gp100 protein, peptides or analogs thereof as the immunogen and bound to a carrier as described above for immune-response-inducing compositions. The host serum or plasma is collected following an appropriate time interval to provide a composition comprising antibodies reactive with the immunogen as is understood by the skilled artisan. The gamma globulin fraction or the IgG antibodies can be obtained, for example, by using saturated ammonium sulfate or DEAE Sephadex, or other techniques known to those skilled in the art. The antibodies are substantially free of many of the adverse side effects which may be associated with other anti-cancer agents such as chemotherapy.

Immunoassays of the present invention may be radioimmunoassay, Western blot assay, immunofluorescent assay, enzyme immunoassay, chemiluminescent assay, immunohistochemical assay and the like. (In "Principles and Practice of Immunoassay" (1991) Christopher P. Price and David J. Neoman (eds), Stockton Press, New York, N.Y.; Ausubel et al. (eds) (1987) in "Current Protocols in Molecular Biology" John Wiley and Sons, New York, N.Y.). Standard techniques known in the art for ELISA are described in *Methods in Immunodiagnosis*, 2nd Edition, Rose and Bigazzi, eds., John Wiley and Sons, N.Y. 1980 and Campbell et al., *Methods of Immunology*, W. A. Benjamin, Inc., 1964, both of which are incorporated herein by reference. Such assays may be direct, indirect, competitive, or noncompetitive immunoassays as described in the art (In "Principles and Practice of Immunoassay" (1991) Christopher P. Price and David J. Neoman (eds), Stockton Pres, New York, N.Y.; Oellirich, M. 1984. *J. Clin. Chem. Clin. Biochem.* 22: 895-904). Biological samples appropriate for such detection assays include mammalian tissues, melanoma and melanocyte cell lines, skin, retina, lymph nodes, pathology specimens, necropsy specimens, and biopsy specimens. Proteins may be isolated from biological samples by conventional methods (see, e.g., Ausubel et al., (eds) (1987) in "Current Protocols in Molecular Biology" John Wiley and Sons, New York, N.Y.).

One skilled in the art will understand that the bioassays or immunoassays of the present invention may be used in the analysis of biological samples or tissues from any vertebrate species. In a preferred embodiment, mammalian biological samples or tissues are analyzed. Tissue includes, but is not limited to, single cells, whole organs and portions thereof. Biological samples include, but are not limited to, tissues, primary mammalian cultures, continuous mammalian cell lines, such as melanocyte cell lines, mammalian organs, such as skin or retina, tissues, biopsy specimens, melanoma and lymph node biopsy samples, neoplasms, pathology specimens, and necropsy specimens. Mammal includes but is not limited to, humans, monkeys, dogs, cats, mice, rats, pigs, cows, pigs, horses, sheep and goats.

Examples of diseases that can be assessed by these immunoassays, include, but are not limited to, melanomas and tissues which are secondary sites for melanoma metastasis. By alteration in level of expression, we mean an increase or decrease of the gp100 protein or portions thereof relative to a control sample. Alteration is also meant to encompass substitution, deletion or addition mutants of the gp100 protein. Such mutations can be determined by using antibodies known to react with specific epitopes of the gp100 protein and determining which epitopes are present relative to a control. These antibodies can therefore be used in an immunoassay to diagnose, assess or prognose a mammal afflicted with the disease.

In a preferred embodiment, the gp100 antibodies are used to assess the presence of the gp100 antigen from a tissue biopsy of a mammal afflicted with melanoma using immunocytochemistry. Such assessment of the delineation of the gp100 antigen in a diseased tissue may be used to prognose the progression of the disease in a mammal afflicted with the disease. Conventional methods for immunohistochemistry are described in Harlow and Lane (eds) (1988) In "Antibodies A Laboratory Manual", Cold Spinning Harbor Press, Cold Spring Harbor, N.Y.; Ausbel et al. (eds) (1987). In Current Protocols In Molecular Biology, John Wiley and Sons (New York, N.Y.).

In yet a further embodiment, the recombinant protein expressed by host cells can be obtained as a crude lysate or can be purified by standard protein purification procedures known in the art which may include differential precipitation, molecular sieve chromatography, ion-exchange chromatography, isoelectric focusing, gel electrophoresis, affinity, and immunoaffinity chromatography and the like. (Ausubel et. al., (1987) in "Current Protocols in Molecular Biology" John Wiley and Sons, New York, N.Y.). Antibodies of this invention can be used to purify the gp100 protein or portions thereof. In the case of immunoaffinity chromatography, the recombinant protein can be purified by passage through a column containing a resin which has bound thereto antibodies specific for the gp100 protein (Ausubel et. al., (1987) in "Current Protocols in Molecular Biology" John Wiley and Sons, New York, N.Y.). A preferred method of purifying gp100 protein can be performed by electrophoresing, collecting, dialyzing, and precipitating the gp100 protein, such that a purity of more than 80% was produced (see Example 10).

The antibodies also can be used as a means of enhancing the immune response. The antibodies can be administered in amounts similar to those used for other therapeutic administrations of antibody. For example, pooled gamma globulin is administered at a range of about 1-100 mg per patient. Thus, antibodies reactive with the gp100 antigen can be passively administered alone or in conjunction with other anti-cancer therapies to a mammal afflicted with melanoma. Examples of anti-cancer therapies include, but are not limited to, chemotherapy, radiation therapy, and adoptive immunotherapy therapy with TIL.

The antibodies or chimeric antibodies described herein also can be coupled to toxin molecules, radio-isotopes, and drugs by conventional methods (Vitetta et al. (1991) in "Biologic Therapy of Cancer" De Vita VT, Hellman S., Rosenberg, S. A. (eds) J. B. Lippincott Co. Philadelphia; and Larson, S. M. et al. (1991) in "Biological Therapy of Cancer" De Vita V. T ., Hellman S., Rosenberg, S. A. (eds) J. B. Lippincott Co., Philadelphia). Examples of toxins to which the antibodies can be coupled to include, but are not limited to, ricin or diphtheria toxin. Examples of drugs or chemotherapeutic agents include, but are not limited to, cyclophosphamide or doxorubcin. Examples of radioisotopes, include, but are not limited to, $^{131}$I. Antibodies covalently conjugated to the aforementioned agents can be used in cancer immunotherapy for treating melanoma.

The antiserum from immunized individuals can be administered as a prophylactic measure for individuals who are at risk of developing melanoma. By "prophylactic" and "prophylaxis" is meant the inhibition or prevention of melanoma. One of ordinary skill in the art readily appreciates that, while complete prevention is desired, any degree of inhibition is can be beneficial. The antiserum is also useful in treating an individual afflicted with melanoma for post-disease prophylaxis.

The gp100 derived proteins and/or peptides of the invention are also intended for use in producing antiserum designed for pre- or post-disease prophylaxis. Here the gp100 antigen, peptides or analogs thereof is formulated with a suitable adjuvant and administered by injection to human volunteers, according to known methods for producing human antisera. Antibody response to the injected proteins is monitored, during a several-week period following immunization, by periodic serum sampling to detect the presence of anti-gp100 serum antibodies, using an immunoassay as described herein.

This invention describes a method of retrovirally transducing dendritic cells (DCs) with the melanoma differentiation antigen gp100, which are then stimulated. The gp100-transduced DCs generated T cells that recognized three distinct HLA-A2 restricted epitopes of the tumor antigen. CD4+ helper T cells specific to a new HLA-DRβ1*0701 epitope of gp100 were generated. The present invention allowed the production of retrovirally-transduced antigen presenting cells (APCs), such as for example, dendritic cells (DCs), to generate T cells reactive against multiple MHC class I and class II epitopes of a tumor antigen which can play a significant role in analysis of tumor antigens and more importantly, for cancer patient immunotherapy. In so doing, a strong immune response against the gp100 antigen was generated.

Additionally provided is a method of transducing APCs with a gp100 nucleic acid sequence comprising: obtaining T cells, for example, CD34+ cells; culturing the T cells with growth factor to stimulate differentiation and proliferation resulting in T cells, such as for example, DCs; and introducing expression vectors, preferably, but not limited to, retroviral vectors and the like, containing all or one or more parts of the gp100 gene, wherein the gp100 gene of interest is expressed. Examples of cells that may be used to deliver nucleic acids encoding gp100 antigens of the present invention include, but are not limited to, T2 cells, (Cerundolo, V. et al. (1990) *Nature,* 345: 449-452) or EBV transformed B cell lines (Topalian et al. (1989) *J. Immunol.* 142: 3714-3725).

In yet another embodiment of this invention, all, part, or parts of the gp100 protein or gp100 peptides can be exposed to dendritic cells (DCs) cultured in vitro. The DCs should be exposed to antigen for sufficient time to allow the antigens to be internalized and presented on the DCs surface (see Example 9). The resulting DCs or the dendritic cell process antigens then can be administered to an individual in need of therapy. In so doing, the cultured DCs provide a means of producing T cell-dependent antigens comprised of dendritic cell-modified antigen or DCs pulsed with antigen, in which the antigen is processed and expressed on the antigen loaded-dendritic cell. The gp100 antigen-loaded DCs may be used as immunogens for vaccines or for the treatment of melanoma. Such methods are described in Steinman et al. (WO93/208185) and in Banchereau et al. (EPO Application 0563485A1), which are incorporated herein by reference.

In yet another embodiment of this invention, T cells isolated from individuals can be exposed to the gp100 protein or portions thereof in vitro and then administered to a patient in need of such treatment in a therapeutically effective amount. Examples of where T-lymphocytes useful in the invention are, include but are not limited to, peripheral blood cell lymphocytes (PBL), lymph nodes, or tumor infiltrating lymphocytes (TIL). Such lymphocytes can be isolated from the individual to be treated or from a donor by methods known in the art and cultured in vitro (Kawakami, Y. et al. (1989) *J. Immunol.* 142: 2453-3461). Lymphocytes are cultured in media such as RPMI or RPMI 1640 or AIM V for 1-10 weeks. Viability is assessed by trypan blue dye exclusion assay. The lymphocytes are exposed to all or part of the gp100 protein for part or all of the culture duration.

In another embodiment, all or parts thereof of a substantially or partially purified gp100 protein and/or gp100 peptide can be administered as an immunogen in a pharmaceutically- and physiologically- acceptable carrier. Ranges of gp100 protein to be administered are 0.001 to 100 mg per patient; preferred doses are 0.01 to 100 mg per patient. Immunization is repeated as necessary, until a sufficient titer of anti-immunogen antibody or immune cells has been obtained. While it is possible for the immunogen to be administered in a pure or substantially pure form, it is preferable to present it as a pharmaceutical composition, formulation or preparation.

In a preferred embodiment, the lymphocytes are exposed to the gp100 peptide of this invention at a concentration of 1-10 micrograms(μg)/ml per $10^7$ cells for all or part of the duration of lymphocyte culture. Peptides can be administered either alone or conjugated. After being sensitized to the peptide, the T lymphocytes are administered to the mammal in need of such treatment. Examples of how these sensitized T cells can be administered to the mammal include, but are not limited to, intravenously, intraperitoneally or intralesionally. Parameters that can be assessed to determine the efficacy of these sensitized T-lymphocytes include, but are not limited to, production of immune cells in the mammal being treated or tumor regression. Conventional methods are used to assess these parameters. Such treatment can be given in conjunction with cytokines or gene modified cells (Rosenberg, S. A., et al. (1992) *Human Gene Therapy,* 3: 75-90; Rosenberg, S. A., et al. (1992) *Human Gene Therapy,* 3: 57-73).

Mammalian cells expressing the gp100 antigen and/or gp100 peptides can be administered to mammals and serve as an immune-response-inducing composition, e.g., vaccine, or immunogen. Examples of how the cells expressing gp100 antigens or peptides can be administered include, but is not limited to, intravenous, intraperitoneal or intralesional. In a preferred embodiment, the entire gp100 nucleic acid sequence is inserted into the gp100 expression vector and introduced into the mammalian cells.

While it is possible for the immunogen to be administered in a pure or substantially pure form, it is preferable to present it as pharmaceutical compositions, formulations or preparations as described above for gp100. Conventional methods can be used to administer the immunogen or immune-response-inducing composition, e.g., vaccine, as previously described above for gp100. The gp100 immunogenic peptides and nucleic acids sequences encoding them can be used in bioassays, or to generate antibodies.

The viral vectors carrying all or part of the gp100 nucleic sequence can be introduced into a mammal either prior to any evidence of melanoma to mediate regression of the disease in a mammal afflicted with melanoma or to prevent the recurrence of disease. Examples of methods for administering the viral vector into the mammals include, but are not limited to, exposure of cells to the virus ex vivo, or injection of the retrovirus or a producer cell line of the virus into the affected tissue or intravenous administration of the virus. For a detailed description of ex vivo gene therapy, see U.S. Pat. No. 5,399,346.

Alternatively, the viral vector carrying all or part of the gp100 nucleic acid sequence can be administered locally by direct injection into the melanoma lesion or topical application in a pharmaceutically acceptable carrier. The quantity of viral vector, carrying all or part of the gp100 nucleic acid sequence, to be administered is based on the titer of virus particles. A preferred range of the immunogen to be administered is $10^6$ to $10^{11}$ virus particles per mammal, preferably a human. After immunization, the efficacy of the vaccine or immunogen can be assessed by production of antibodies or immune cells that recognize the antigen, as assessed by specific lytic activity or specific cytokine production or by tumor regression. One skilled in the art is aware of conventional methods to assess the aforementioned parameters. If the mammal to be immunized is already afflicted with melanoma or metastatic melanoma, the vaccine can be administered in conjunction with other therapeutic treatments. Examples of other therapeutic treatments include, but are not limited to, adoptive T cell immunotherapy, coadministration of cytokines, or other therapeutic drugs for melanoma.

The pharmaceutical compositions or formulations of the present invention, both for veterinary and for human use, comprise a gp100 protein, gp100 peptide, and/or immunogen as described herein, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations can conveniently be presented in unit dosage form and can be prepared by any method well known in the pharmaceutical art. Carriers can also include, but are not limited to excipients and/or diluents.

In a preferred embodiment of the invention, a vaccine or immunogenic formulation comprising an immunogen that induces an immune response directed against the melanoma associated antigen, gp100, is provided. The gp100 formulations are evaluated first in animal models, initially rodents, and in nonhuman primates and then in humans. The safety of the immunization procedures is determined by looking for the effect of immunization on the general health of the immunized animal (weight change, fever, appetite behavior, etc.) and looking for pathological changes on autopsies. After initial testing in animals, melanoma cancer patients are tested. Conventional methods are used to evaluate the immune response of the patient to determine the efficiency of the vaccine.

The formulations of the present invention can incorporate a stabilizer. Illustrative stabilizers are polyethylene glycol, proteins, saccharides, amino acids, inorganic acids, and organic acids which can be used either on their own or as admixtures. These stabilizers are preferably incorporated in an amount of 0.11-10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of 0.1-3.0 osmoles, preferably in the range of 0.8-1.2. The pH of the aqueous solution is adjusted to be within the range of 5.0-9.0, preferably within the range of 6-8. In formulating the immunogen of the present invention, anti-adsorption agent may be used.

When oral preparations are desired, the compositions can be combined with typical carriers, such as lactose, sucrose, starch, talc magnesium stearate, crystalline cellulose, methyl cellulose, carboxymethyl cellulose, glycerin, sodium alginate or gum arabic among others.

All methods include the step of bringing into association the active ingredient with the carrier, which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous, intramuscular, subcutaneous, or intraperitoneal administration conveniently comprise sterile aqueous solutions of the active ingredient with solutions which are preferably isotonic with the blood of the recipient. Such formulations can be conveniently prepared by dissolving solid active ingredient in water containing physiologically compatible substances, such as sodium chloride (e.g. 0.1-2.0 M), glycine, and the like, and having a buffered pH compatible with physiological conditions to produce an aqueous solution, and rendering said solution sterile. These can be present in unit or multi-dose containers, for example, sealed ampoules or vials.

Additional pharmaceutical methods can be employed to control the duration of action. Controlled release preparations can be achieved through the use of polymer to complex or absorb the proteins or their derivatives. The controlled delivery can be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the gp100 protein, peptides and analogs thereof into particles of a polymeric material, such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

Local administration to the afflicted site can be accomplished through means known in the art, including, but not limited to, topical application, injection, and implantation of a porous device containing cells recombinantly expressing the infusion, implantation of a porous device in which the gp100 antibodies or chimeric antibodies, antibodies coupled to toxins, drugs or radiolabels or portions thereof are contained.

When used as a means of inducing gp100 antibodies in an animal, the manner of injecting the antibody is the same as for vaccination purposes, namely intramuscularly, intraperitoneally, subcutaneously, interlesionally, or the like in an effective concentration in a physiologically suitable diluent with or without adjuvant. One or more booster injections may be desirable.

The proteins of the present invention can be supplied in the form of a kit, alone, or in the form of a pharmaceutical composition as described above.

The above described antibodies and antigen-binding fragments thereof can be supplied in kit form alone, or as a pharmaceutical composition for in vivo use. The antibodies can be used for therapeutic uses, diagnostic use in immunoassays, or as an immunoaffinity agent to purify the gp100 protein or peptides as described herein.

All books, articles, and patents referenced herein are incorporated by reference in toto. The following examples illustrate various aspects of the invention and in no way intended to limit the scope thereof.

EXAMPLE 1

Media and Cell Culture

Complete medium consisted of Iscove's (Biofluids Inc.; Rockville, Md. and Life Technologies; Gaithersburg, Md.) supplemented with 10% human AB serum (male,. heat inactivated; Gemini Bio-Products, Calabasas, Calif.), 1 mM glutamine, 50 U/ml penicillin, 50 µg/ml streptomycin (all from Biofluids Inc.) and 50 µg/ml gentamicin (Life Technologies). DC medium consisted of complete medium supplemented with 100 ng/ml of GM-CSF, 100 ng/ml of TNF-$\alpha$ (both from Peprotech, Rocky Hill, N.J.) and 40 ng/ml of stem cell factor (SCF; R&D System Inc., Minneapolis, Minn.). T cell medium consisted of complete medium supplemented with 60 to 300 IU/ml rIL-2 (Chiron; Emeryville, Calif.). T cell clones and TIL 1520 were cultured in AIM-V medium (Life Technology) supplemented with 5% human serum and 1 mM glutamine, 50 U/ml penicillin, 50 µg/ml streptomycin and 50 µg/ml gentamicin. rIL-2 at a concentration 6,000 IU/ml was added for TIL 1520 and 300 IU/ml for the T cell clones.

The melanoma cell line from patient A was developed at the Surgery Branch NCI/NIH; (Topalian et al. *Proc. Natl. Acad. Sci. USA*. 91:9461-65, 1994). Since the melanoma line from patient A failed to express gp100, this line was transduced using a VSV-pseudotyped retroviral vector expressing either gp100 or green fluorescent protein (GFP). EBV-immortalized B cells were generated as previously described (Topalian et al. *Proc. Natl. Acad. Sci. USA*. 91:9461-65, 1994). Transduced cells were cultured in RPMI-based medium containing 500 µg/ml of geneticin sulfate (Life Technologies). All tumor and EBV-B cell lines were grown in RPMI 1640 medium (Life Technologies) supplemented with 10% heat inactivated FBS (Biofluids Inc. and Life Technologies) and antibiotics.

CD34$^+$ hematopoietic progenitor cells (HPC) were obtained from HLA-A2 positive patients undergoing treatment for melanoma as part of an Institutional Review Board-approved protocol (Surgery Branch, NCI). CD34$^+$ cells were mobilized in peripheral blood by five daily s. c. injections of 10 µg/kg granulocyte colony-stimulating factor (Neupogen, Amgen, Thousand Oaks, Calif.), followed by a lymphocytopheresis to obtain PBMCs on day 6. CD34$^+$ cells were selected by an immunoaffinity column (CellPro Inc., Bothed, Wash.) and cryopreserved. A single leukapheresis typically yielded 2-5×10$^8$ CD34$^+$ cells.

EXAMPLE 2

Retroviral Vectors

The PG13-based gp100 retroviral packaging cell line was generated by inserting the complete gp100 CDNA into the retroviral vector SAMEN (Kershaw et al. *Hum. Gene Ther.* 11:2445-52, 2000) as described previously (Reeves et al. *Cancer Res.* 56:5672-5677, 1996). Producer cell medium consisted of Dulbecco's Modified Eagle Medium (Life Technologies) supplemented with 10% heat inactivated FBS and antibiotics.

The gp100-VSV-pseudotyped retroviral system was prepared by first inserting the complete gp100 sequence in the pCLNC retroviral plasmid (Naviaux et al. *J. Virol.* 70:5701-5705, 1996)(28). The pCLNC-gp100 and pMDG-VSV plasmids were co-transfected in 293-gag-pol packaging cells using Lipofectamine Plus (Life Technologies). The 293-gag-pol packaging cells (Salk Institute; La Jolla, Calif.), were cultured in DMEM supplemented with 10% heat inactivated FBS and antibiotics. Medium was changed 16 hours and 48 hours after transfection. Culture supernatants were harvested on days 3 and 4 after transfection of the 293-gag-pol cells. Producer cells were removed from retroviral supernatant by filtration with 0.2 µm filter (Nalgene; Rochester, N.Y.). Supernatants were immediately frozen at −70° C. for future use.

EXAMPLE 3

Transduction of CD34+ Derived Dendritic Cells

CD34$^+$ cells were differentiated to dendritic cells according to the protocol previously described (Reeves et al. *Cancer Res.* 56:5672-5677, 1996). Briefly, CD34$^+$ cells were thawed, washed in complete medium and plated at 5×10$^6$ cells/well in a 6 well plate or 5×10$^5$ cells/well in a 24 well plate in complete DC medium containing TNF-$\alpha$, SCF and GM-CSF. Cultured cells were harvested on days 5 and 10, centrifuged and resuspended in complete DC medium with cytokines. Cells were utilized on day 14 and DC phenotype was confirmed by morphological and FACS analyses (Reeves et al. *Cancer Res.* 56:5672-5677, 1996).

For transduction with the PG13 system, CD34$^+$ cells were co-cultured with irradiated PG13-SAM-gp100-EN producer cells (31 Gy; 7×10$^5$ cells/well in 6 well plate) in complete DC medium with cytokines containing 8 µg/ml of polybrene (Aldrich Chemical Co., Milwaukee, Wis.). After 30 h, DCs were replated on fresh irradiated producer cells in DC medium including cytokines without polybrene for 24 h. On day 3, transduced DCs were resuspended in fresh complete DC medium in a 6 well plate and the differentiation was completed as described earlier.

For transduction with the VSV-pseudotyped retroviruses, retroviral supernatant was added to cultured CD34$^+$ cells on days 2 and 3 at a ratio of 1:1 with culture medium. GM-CSF, SCF, TNF-$\gamma$ and polybrene were added and cells were spun in the plate at 1,000×g for one hour. On day 4, transduced DCs were resuspended in fresh complete DC medium in a 6 well plate and the differentiation was completed as described above.

EXAMPLE 4

Stimulation of Autologous T Lymphocytes with Transduced Dendritic Cells

Autologous human PBMC (peripheral blood mononuclear cells) were obtained from leukapheresis of patients at the Surgery Branch (NCI) and cryopreserved for use in experiments. T lymphocytes were isolated from PBMC using a human T cell immunoaffinity column (R&D Inc). Purified T cells (2×10$^6$) were co-cultured with irradiated gp100-transduced DCs (2×10$^5$, 15 Gy) in a 24 well plate in 2 ml of complete medium without rIL-2. rIL-2 (60 to 300 U/ml) was added on day 2 and the cells were diluted with fresh complete medium and rIL-2 to keep the cell concentration at 1-2×10$^6$ cell/ml. T cells from patient A were obtained prior to any non-surgical treatment of melanoma and were stimulated once with gp100-transduced DCs. T lymphocytes from patient B were obtained eight months after immunization with gp100$_{280-288}$ peptide in incomplete Freund's adjuvant (Salgaller et al. *Cancer Res.* 56:4749-4757, 1996). In some cultures, a combination of soluble trimeric recombinant CD40L (Immunex Corporation, Seattle, Wash.) and lipopolysaccharide prepared from *Salmonella typhimurium* (Sigma Chemical Co., St-Louis, Mo.) were added to the T cell stimulation with the gp100-transduced DCs. CD40L and LPS can increase the capacity of DCs to stimulate the generation of antigen-specific T cells (Lapointe et al. *Eur. J. Immunol.* 30:3291-3298, 2000).

In addition to presentation of epitopes by MHC class I, transduced DCs may present peptides in the context of MHC class II molecules. T cell stimulations were next performed to determine whether gp100-transduced DCs could generate antigen-specific CD4⁺ T cells recognizing gp100 peptides presented by MHC class II. T cells from patient A were stimulated twice with DCs retrovirally transduced with gp100. Stimulated T cells were analyzed for their capacity to recognize a gp100 expressing autologous melanoma cell line in an MHC class II restricted fashion. The cultured T cells were reactive against the autologous tumor line expressing HLA-DR and gp100 but not against gp100-negative melanoma cells or autologous cultured B cells.

The reactive bulk T cell culture was cloned by limiting dilution and wells containing growing cells were screened using autologous melanoma cells expressing gp100 or GFP as a negative control. The bulk T cell cultures were cloned by limiting dilution at 1, 2 or 10 cells/well in 96 round bottom well plates (Dudley et al. *J. Immunother.* 22:288-298, 1999). Cloning was done in complete medium using AIM-V medium supplemented with 5% human AB serum, 1 mM glutamine, 50 U/ml penicillin, 50 µg/ml streptomycin and 50 µg/ml gentamicin in the presence of 5×10⁴ irradiated PBMC prepared from 3 different donors (from normal volunteers at the Clinical Center, NIH), 30 ng/ml of anti-CD3 (OKT3; Ortho-Biotech, Raritan, N.J.) and 300 U/ml of rIL-2. Relevant clones were expanded in T-25 tissue culture flasks at 1 to 5×10⁵ cells/flask with 2.5×10⁷ irradiated PBMC feeders prepared from 3 different donors (Blood bank, Clinical center, NIH) and 30 ng/ml of anti-CD3 in 25 ml of AIM-V complete medium. On day 2, 300 U/ml of rIL-2 was added and on day 5, 20 ml of medium was replaced with fresh AIM-V complete medium containing 300 U/ml of rIL-2. On day 8, cells were counted and the cell concentration was maintained at 1 to 2×10⁶ cells/ml in AIM-V complete medium with 300 U/ml of rIL-2.

Figure 2:
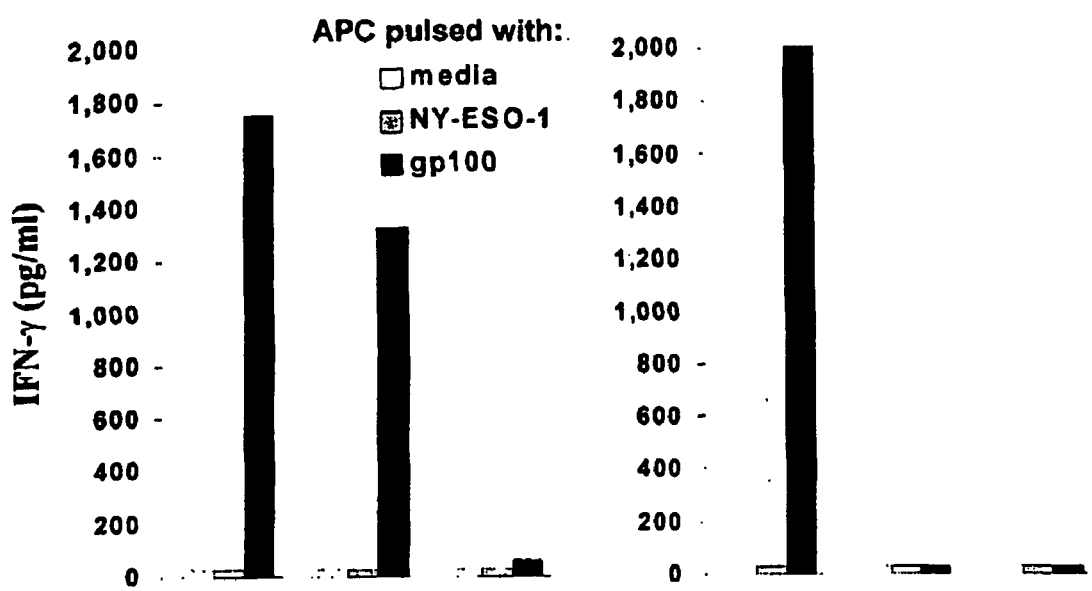
FIG. 2 shows specific recognition by a T cell clone of HLA-DR matched B cells pulsed with purified gp100. T cells were co-cultured with EBV-B cells prepared from donors sharing different HLA-DR alleles after a 16 h pulsing with purified proteins (NY-ESO-1 or gp100). Results are expressed in pg/ml of IFN-γ released following a 24 h co-culture.

Forty-six of 167 wells were found to be specifically reactive against the autologous melanoma expressing gp100 and class II. The reactivity of nine representative positive clones is presented in FIG. 1A along with 4 representative negative wells (neg1 to neg4). Eight of the 46 positive clones were expanded and further characterized. All 8 clones were CD4⁺ suggesting recognition of gp100 peptides presented by MHC class II. To further characterize the reactivity, some of the clones were co-cultured with autologous B cells pulsed with a bacterially produced gp100 protein. All the CD4⁺ T cell clones tested secreted IFN-γ when exposed to autologous B cells pulsed with gp100 but not those pulsed with an irrelevant tumor antigen prepared using a similar procedure. The results from two representative clones are presented in FIG. 1B. Clones 6 and 8 failed to react against NY-ESO-1, a protein produced similarly to the recombinant gp100. In order to identify the MHC restriction element, antibodies known to bind and block the presentation by defined MHC molecules were used. Recognition by clones 6 and 8 of target cells pulsed with the gp100 protein was inhibited when using blocking antibodies against MHC class II and HLA-DR but the recognition was unchanged when using a blocking MHC class I antibody. Also, both clones failed to recognize gp100 when pulsed on un-matched HLA-DR B cells. By using HLA-DR matched B cells, the restriction element was identified as HLA-DRβ1*0701 (patient A is HLA-DRβ1*0701 and *1601; FIG. 2).

Figure 3:
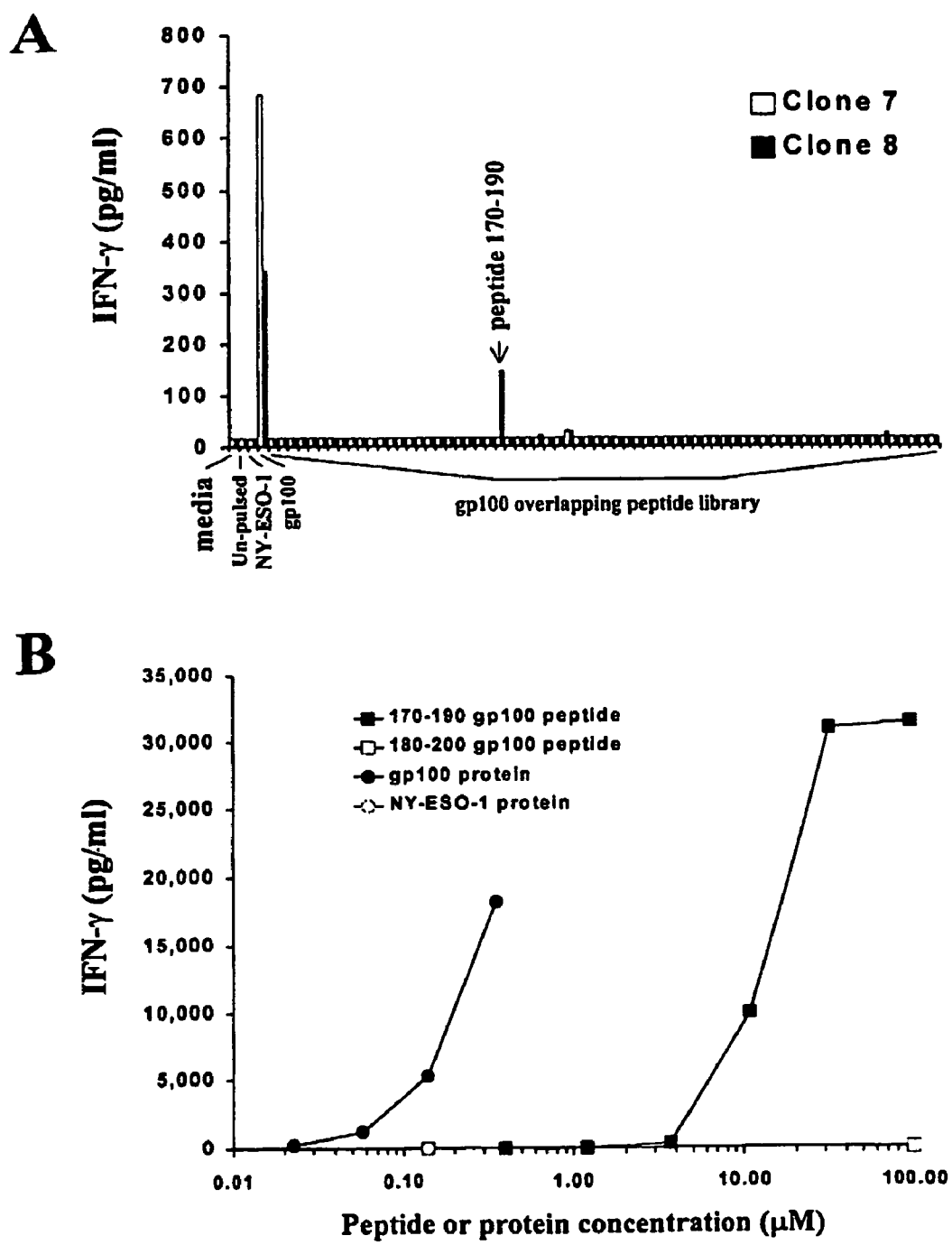
FIGS. 3A and 3B show the identification of an HLA-DRβ1*0701 gp100-epitope using an overlapping peptide library. (A) T cell clones 7 and 8 were co-cultured with autologous EBV-B cells pulsed with NY-ESO-1 or gp100 proteins (10 µg/ml) or 68 overlapping peptides derived from gp100 (all at 100 µM). (B) A $gp100_{170-190}$-specific T cell clone was co-cultured with autologous EBV-B cells after pulsing with gp100 protein or the $gp100_{170-190}$ peptide at different concentrations. Results are expressed in pg/ml of IFN-γ release following a 24 h co-culture.

To find the epitope recognized, an overlapping gp100 peptide library consisting of 68 peptides of 17 or 21 residues overlapping by 10-12 amino acids was prepared. The autologous EBV-B cells were pulsed with the peptide library and used as targets in a T cell recognition assay using three different T cell clones. Two clones failed to recognize any peptides and one clone specifically recognized peptide gp100$_{170-190}$ (FIG. 3A; data from two clones shown). Using a gp100$_{170-190}$-specific T cell clone, a titration experiment using the gp100$_{170-190}$ peptide pulsed on EBV-B cells revealed that the recognition was undetectable below 4-10 µM (FIG. 3B). Interestingly, the gp100$_{170-190}$-specific T cell clone recognized B cells pulsed with gp100 protein at a concentration as low as 22 nM.

Finally, several peptides were synthesized in order to define an optimal HLA-DRβ1*0701 epitope (Rammensee, H. G. *Immunogenetics* 41:178-228, 1995; Chicz et al. *J. Exp. Med.* 178:27-47, 1993). As shown in table 1, no peptides were better recognized at 10 or 1 µM compared with the gp100$_{170-190}$ peptide. Finally, substitutions were made at position 5 of the gp100$_{174-194}$ peptide presuming that this is position 1 according to the defined motif for HLA-DRβ1*0701 (SYFPEITHI web site, http://syfpeithi.de/). However, none of the peptides were better recognized when pulsed at 10 µM or 1 µM compared to the wild type gp100$_{174-194}$ peptide.

The data presented demonstrate that CD34-derived dendritic cells retrovirally-transduced with gp100 can generate T cells reactive against MHC class II gp100 epitopes.

EXAMPLE 5

T Cell Assays

The gp100 peptide library consisted of 68 peptides of 17 to 21 residues overlapping by 10 to 12 amino acids. The peptides were synthesized by solid phase FMOC methodology as previously described (Parkhurst et al. *J. Immunol.* 157:2539-2548, 1996). A control peptide derived from the Ig kappa chain known to bind to HLA-DRβ1*0701 was also prepared (Chicz et al. *J. Exp. Med.* 178:27-47, 1993). Recombinant gp100 protein was made and purified as previously described Touloukian et al. *J. Immunol.* 164:3535-3542, 2000). Recombinant NY-ESO-1 protein is another tumor antigen (Chen, YT and LJ Old. *Cancer J. Sci. Am.* 5:16-17, 1999) used as negative control and was made and purified as previously described (Zeng et al. *J. Immunol.* 165:1153-1159, 2000). EBV-B cells (1×10⁵) were pulsed with gp100-purified protein or peptides for 18 hours in 96 well flat-bottom plates and T cells were added directly to the pulsed-B cells for a 24 hours recognition assay. In some experiments, EBV-B cells (5×10⁵) were pulsed in 48 well plates for 18 hours and cells were washed twice with PBS. T cells were then co-cultured with the pulsed EBV-B cells in 96 well flat-bottom plates for 24 hours. Supernatants were harvested and human IFN-γ was assayed by ELISA using a commercially available kit (R&D Inc.).

EXAMPLE 6

IFN-γ Release Assay

Fifty to one hundred thousand responder cells and 4×10⁴-10⁵ stimulator cells were mixed in 300 ul of AIM-V medium containing 120IU/ml IL-2 per well in a 96 flat-well microplate. Target cells (1×10⁵) were incubated with 1×10⁵ specific T cells in 250 µl of T cell medium (AIM-V-based medium) in 96 well flat-bottom plates. Supernatants were harvested after 24 h and human IFN-γ was assayed by ELISA using a commercially available kit (R&D, Inc.; Minneapolis, Minn.).

EXAMPLE 7

GP100 Immunogens as a Treatment for Melanoma in Mammals

Gp100 immunogens may be efficacious in treating mammals afflicted with melanoma. For example, gp100 immune-response-inducing compositions may be administered to individuals. Mammals are immunized with the recombinant proteins in the range of 1 mg-100 mg. Alternatively, patients, are immunized with the gp100 nucleic acid sequence inserted into a viral vector such as vaccinia virus, adenovirus or fowl pox virus. A range of about $10^6$-$10^{11}$ viral particles carrying the gp100 nucleic acid sequences are administered per patient. The patients are monitored for antibodies to the immunogen or increase in cytotoxic lymphocytes (CTL) recognizing the immunogen by conventional methods or alleviation of clinical signs and symptoms of the active disease. Specific parameters to be assessed include production of immune cells that recognize the vaccine antigen or tumor regression. Such immune-response-inducing compositions are administered either prophylactically or therapeutically. Alternatively, patients are immunized with the gp100 nucleic acid sequence inserted into a retroviral vector. Suggested dose ranges of the antigen in retroviruses are $10^6$-$10^{11}$ viral particles per patient. Response and efficacy of the retroviral vaccines are assessed as described above.

EXAMPLE 8

Use of Lymphocytes Sensitized to Immunogenic Peptides Derived from Melanoma Antigens for Therapeutically Treating Patients Afflicted with Melanoma T-lymphocytes presensitized to the melanoma antigen are effective in therapeutically treating patients afflicted with melanoma. The T-lymphocytes are isolated from peripheral blood lymphocytes or tumor infiltrating lymphocytes and exposed in vitro to the gp100 protein or peptide. T-lymphocytes are isolated from peripheral blood or melanoma tumor suspensions and cultured in vitro (Kawakami, Y. et al. (1988) *J. Exp. Med.* 168: 2183-2191). The T-lymphocytes are stimulated with 1 to 10 µg/ml of the gp100-derived peptide and cultured for 2 to 6 weeks to get a high number of cells (Dudley, M. et al. (1999) *J. Immunother.* 22:288-298). T-lymphocytes exposed to the antigen are administered to the patient at about $10^9$-$10^{12}$ lymphocytes per patient. The lymphocytes may be administered either intravenously, intraperitoneally or intralesionally. This treatment may be administered concurrently with other therapeutic treatments such as cytokines, radiotherapy, surgical excision of melanoma lesions, and chemotherapeutic drugs.

EXAMPLE 9

Recombinant Human GP100 Protein

The gene encoding human gp100 (h-gp100; Kawakami, et al. *Proc. Natl. Acad. Sci. USA* 91:6458, 1994) was amplified by PCR with primers (forward: 5'-AGGCGCAGACTTAT-GAAGCA-3' (SEQ ID NO:24); reverse: 5'-CTGCCCAAG-GCCTGCTTCTTG-3' (SEQ ID NO:25)) designed to delete the N-terminal 23 amino acids (probable signal sequence) and the C-terminal 66 amino acids (probable transmembrane region). The truncated gene was then cloned into the PET28a⁺ expression vector (Novagen; Madison, Wis.) and transformed into BL21(DE3) *Escherichia coli* (Novagen). *E. coli* were grown to OD600 0.6, then protein expression was induced with isopropyl β-D-thiogalactoside 1 µg/ml for 3 h. The bacteria were harvested; inclusion bodies were isolated and lysed in 6 M urea, then proteins were purified by preparative scale SDS-PAGE in a Prep cell (Bio-Rad; Hercules, Calif.) electrophoresis chamber. Protein fractions at 61.5 kDa (theorectical molecular mass of truncated h-gp100) were collected, dialyzed, and precipitated, and a purity of more than 80% was estimated based on SDS-PAGE with Colloidal Blue (Novex; San Diego, Calif.) staining.

The present invention is not to be limited in scope by the nucleic acid sequences deposited, since the deposited embodiments is intended as a single illustration of one aspect of the invention and any sequences which are functionally equivalent are within the scope of this invention. Indeed, various modifications of the invention in addition to those shown and described herein will become apparent to those skilled in the art from the foregoing description and accompanying drawings. Such modifications are intended to fall within the scope of the dependent claims. It is also to be understood that all base pair sizes given for nucleotides are approximated and are used for purpose of description.

---

What is claimed is:

1. An immunogenic peptide consisting of a gp100 amino acid sequence selected from LSIGTGRAMLGTHTMEVTVYH (SEQ ID NO:3), IGTGRAMLGTHTMEVTVYHRR (SEQ ID NO:4), TGRAMLGTHTMEVTVYHRRGS (SEQ ID NO:5), TGRAMLGTHTMEVTVYHR (SEQ ID NO:6), TGRAMLGTHTMEVTVYHRR (SEQ ID NO:7), TGRAMLGTHTMEVTVYHRRG (SEQ ID NO:8), GTGRAMLGTHTMEVTVYHRRG (SEQ ID NO:9), GTGRAMLGTHTMEVTVYH (SEQ ID NO:10), IGTGRAMLGTHTMEVTVYH (SEQ ID NO:11), SIGTGRAMLGTHTMEVTVYH (SEQ ID NO:12), or SIGTGRAMLGTHTMEVTVYHR (SEQ ID NO:13), TGRAFLGTHTMEVTVYHRRGS (SEQ ID NO:17), TGRALLGTHTMEVTVYHRRGS (SEQ ID NO:18), or TGRAYLGTHTMEVTVYHRRGS (SEQ ID NO:19), wherein said peptide is reactive with T cells or induces an immune response.

2. The immunogenic peptide of claim 1, wherein said peptide is recognized by HLA-DRβ1*0701 restricted T cells.

3. A pharmaceutical composition comprising an immunogenic peptide and a pharmaceutically-acceptable carrier therefore, wherein said peptide consists of a gp100 amino acid sequence selected from any of SEQ ID NOs: 3-13 and 17-19, wherein said peptide is reactive with T cells or induces an immune response.

4. A method of determining immunogenicity of a peptide selected from a gp100 amino acid sequence consisting of any of SEQ ID NOs: 3-13 and 17-19, wherein said peptide is reactive with T cells, comprising: a) incubating the peptide with mammalian cells; b) exposing the mammalian cells incubated with the immunogenic peptide to T cells; and c) screening for T cell recognition of the peptide using the mammalian cells incubated with the immunogenic peptide, whereupon the immunogenicity of the peptide is determined.

5. An immunogenic peptide with a gp100 amino acid sequence consisting of TGRAMLGTHTMEVTVYH (SEQ ID NO:2), or a variant thereof, wherein the variant consists of SEQ ID NO:2 with an amino acid substitution in which the fifth amino acid of SEQ ID NO:2 is replaced with a Phe, Leu, or Tyr, or an amino acid which is a conservative substitution thereof, wherein said peptide or variant thereof is reactive with T cells or induces an immune response.

6. The immunogenic peptide of claim 5, wherein said peptide or variant is recognized by HLA-DRβ1*0701 restricted T cells.

7. A pharmaceutical composition comprising an immunogenic peptide and a pharmaceutically-acceptable carrier therefor, wherein said peptide includes a gp100 amino acid sequence consisting of TGRAMLGTHTMEVTVYH (SEQ ID NO:2), or a variant thereof, wherein the variant consists of SEQ ID NO:2 with an amino acid substitution in which the fifth amino acid of SEQ ID NO:2 is replaced with a Phe, Leu, or Tyr, or an amino acid which is a conservative substitution thereof, wherein said peptide or variant thereof is reactive with T cells or induces an immune response.

8. A method of determining immunogenicity of a peptide with a gp100 amino acid sequence consisting of TGRAMLGTHTMEVTVYH (SEQ ID NO:2), or a variant thereof, wherein the variant consists of SEQ ID NO:2 with an amino acid substitution in which the fifth amino acid of SEQ ID NO:2 is replaced with a Phe, Leu, or Tyr, or an amino acid which is a conservative substitution thereof, wherein said peptide or variant thereof is reactive with T cells, comprising: a) incubating the peptide or variant with mammalian cells; b) exposing the mammalian cells incubated with the immunogenic peptide or variant to T cells; and c) screening for T cell recognition of the peptide or variant using the mammalian cells incubated with the immunogenic peptide or variant, whereupon the immunogenicity of the peptide is determined.

* * * * *

SEQUENCE LISTING

<160> NUMBER OF SEQ ID NOS: 21

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Met Leu Gly Thr His Thr Met Glu Val Thr Val
1               5                   10

<210> SEQ ID NO 2

```
<211> LENGTH: 17
<212> TYPE: PRT
<213> ORGANISM: Artificial Sequence
<220> FEATURE:
<223> OTHER INFORMATION: Synthetic

<400> SEQUENCE: 2

Thr Gly Arg Ala Met Leu Gly Thr His Thr Met Glu Val Thr Val Tyr
1               5                   10                  15

His

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

Leu Ser Ile Gly Thr Gly Arg Ala Met Leu Gly Thr His Thr Met Glu
1               5                   10                  15

Val Thr Val Tyr His
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic

<400> SEQUENCE: 4

Ile Gly Thr Gly Arg Ala Met Leu Gly Thr His Thr Met Glu Val Thr
1               5                   10                  15

Val Tyr His Arg Arg
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic

<400> SEQUENCE: 5

Thr Gly Arg Ala Met Leu Gly Thr His Thr Met Glu Val Thr Val Tyr
1               5                   10                  15

His Arg Arg Gly Ser
            20

<210> SEQ ID NO 6
<211> LENGTH: 18
<212> TYPE: PRT
<213> ORGANISM: Artificial Sequence
<220> FEATURE:
<223> OTHER INFORMATION: Synthetic

<400> SEQUENCE: 6

Thr Gly Arg Ala Met Leu Gly Thr His Thr Met Glu Val Thr Val Tyr
1               5                   10                  15

His Arg

<210> SEQ ID NO 7
<211> LENGTH: 19
```

```
<212> TYPE: PRT
<213> ORGANISM: Artificial Sequence
<220> FEATURE:
<223> OTHER INFORMATION: Synthetic

<400> SEQUENCE: 7

Thr Gly Arg Ala Met Leu Gly Thr His Thr Met Glu Val Thr Val Tyr
1               5                   10                  15

His Arg Arg

<210> SEQ ID NO 8
<211> LENGTH: 20
<212> TYPE: PRT
<213> ORGANISM: Artificial Sequence
<220> FEATURE:
<223> OTHER INFORMATION: Synthetic

<400> SEQUENCE: 8

Thr Gly Arg Ala Met Leu Gly Thr His Thr Met Glu Val Thr Val Tyr
1               5                   10                  15

His Arg Arg Gly
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic

<400> SEQUENCE: 9

Gly Thr Gly Arg Ala Met Leu Gly Thr His Thr Met Glu Val Thr Val
1               5                   10                  15

Tyr His Arg Arg Gly
            20

<210> SEQ ID NO 10
<211> LENGTH: 18
<212> TYPE: PRT
<213> ORGANISM: Artificial Sequence
<220> FEATURE:
<223> OTHER INFORMATION: Synthetic

<400> SEQUENCE: 10

Gly Thr Gly Arg Ala Met Leu Gly Thr His Thr Met Glu Val Thr Val
1               5                   10                  15

Tyr His

<210> SEQ ID NO 11
<211> LENGTH: 19
<212> TYPE: PRT
<213> ORGANISM: Artificial Sequence
<220> FEATURE:
<223> OTHER INFORMATION: Synthetic

<400> SEQUENCE: 11

Ile Gly Thr Gly Arg Ala Met Leu Gly Thr His Thr Met Glu Val Thr
1               5                   10                  15

Val Tyr His

<210> SEQ ID NO 12
<211> LENGTH: 20
<212> TYPE: PRT
<213> ORGANISM: Artificial Sequence
```

```
<220> FEATURE:
<223> OTHER INFORMATION: Synthetic

<400> SEQUENCE: 12

Ser Ile Gly Thr Gly Arg Ala Met Leu Gly Thr His Thr Met Glu Val
1               5                   10                  15

Thr Val Tyr His
            20

<210> SEQ ID NO 13
<211> LENGTH: 21
<212> TYPE: PRT
<213> ORGANISM: Artificial Sequence
<220> FEATURE:
<223> OTHER INFORMATION: Synthetic

<400> SEQUENCE: 13

Ser Ile Gly Thr Gly Arg Ala Met Leu Gly Thr His Thr Met Glu Val
1               5                   10                  15

Thr Val Tyr His Arg
            20

<210> SEQ ID NO 14
<211> LENGTH: 21
<212> TYPE: PRT
<213> ORGANISM: Artificial Sequence
<220> FEATURE:
<223> OTHER INFORMATION: Synthetic

<400> SEQUENCE: 14

Ser Gly Leu Ser Ile Gly Thr Gly Arg Ala Met Leu Gly Thr His Thr
1               5                   10                  15

Met Glu Val Thr Val
            20

<210> SEQ ID NO 15
<211> LENGTH: 21
<212> TYPE: PRT
<213> ORGANISM: Artificial Sequence
<220> FEATURE:
<223> OTHER INFORMATION: Synthetic

<400> SEQUENCE: 15

Arg Ala Met Leu Gly Thr His Thr Met Glu Val Thr Val Tyr His Arg
1               5                   10                  15

Arg Gly Ser Arg Ser
            20

<210> SEQ ID NO 16
<211> LENGTH: 21
<212> TYPE: PRT
<213> ORGANISM: Artificial Sequence
<220> FEATURE:
<223> OTHER INFORMATION: Synthetic

<400> SEQUENCE: 16

Met Leu Gly Thr His Thr Met Glu Val Thr Val Tyr His Arg Arg Gly
1               5                   10                  15

Ser Arg Ser Tyr Val
            20

<210> SEQ ID NO 17
<211> LENGTH: 21
<212> TYPE: PRT
```

```
<213> ORGANISM: Artificial Sequence
<220> FEATURE:
<223> OTHER INFORMATION: Synthetic

<400> SEQUENCE: 17

Thr Gly Arg Ala Phe Leu Gly Thr His Thr Met Glu Val Thr Val Tyr
1               5                   10                  15

His Arg Arg Gly Ser
            20

<210> SEQ ID NO 18
<211> LENGTH: 21
<212> TYPE: PRT
<213> ORGANISM: Artificial Sequence
<220> FEATURE:
<223> OTHER INFORMATION: Synthetic

<400> SEQUENCE: 18

Thr Gly Arg Ala Leu Leu Gly Thr His Thr Met Glu Val Thr Val Tyr
1               5                   10                  15

His Arg Arg Gly Ser
            20

<210> SEQ ID NO 19
<211> LENGTH: 21
<212> TYPE: PRT
<213> ORGANISM: Artificial Sequence
<220> FEATURE:
<223> OTHER INFORMATION: Synthetic

<400> SEQUENCE: 19

Thr Gly Arg Ala Tyr Leu Gly Thr His Thr Met Glu Val Thr Val Tyr
1               5                   10                  15

His Arg Arg Gly Ser
            20

<210> SEQ ID NO 20
<211> LENGTH: 21
<212> TYPE: PRT
<213> ORGANISM: Artificial Sequence
<220> FEATURE:
<223> OTHER INFORMATION: Synthetic

<400> SEQUENCE: 20

Pro Val Ser Gly Leu Ser Ile Gly Thr Gly Arg Ala Met Leu Gly Thr
1               5                   10                  15

His Thr Met Glu Val
            20

<210> SEQ ID NO 21
<211> LENGTH: 16
<212> TYPE: PRT
<213> ORGANISM: Artificial Sequence
<220> FEATURE:
<223> OTHER INFORMATION: Synthetic

<400> SEQUENCE: 21

Thr Thr Glu Trp Val Glu Thr Thr Ala Arg Glu Leu Pro Ile Pro Glu
1               5                   10                  15
```